United States Patent [19]

Cooke et al.

[11] Patent Number: 4,574,794
[45] Date of Patent: Mar. 11, 1986

[54] ORTHOPAEDIC BONE CUTTING JIG AND ALIGNMENT DEVICE

[75] Inventors: Theodore D. Cooke, Kingston; Gerald A. B. Saunders, Sydenham; David Siu, Kingston, all of Canada

[73] Assignee: Queen's University at Kingston, Kingston, Canada

[21] Appl. No.: 616,068

[22] Filed: Jun. 1, 1984

[51] Int. Cl.⁴ .............................................. A61F 5/04
[52] U.S. Cl. ............................ 128/92 H; 128/92 EB
[58] Field of Search ............... 128/92 H, 92 R, 92 E, 128/92 EB, 303 R

[56] References Cited

U.S. PATENT DOCUMENTS

| | | | |
|---|---|---|---|
| 4,457,307 | 7/1984 | Stillwell | 128/92 EB |
| 4,474,177 | 10/1984 | Whiteside | 128/92 H |
| 4,487,203 | 12/1984 | Androphy | 128/92 H |
| 4,524,766 | 6/1985 | Petersen | 128/92 E |

Primary Examiner—Robert Peshock
Assistant Examiner—C. W. Shedd
Attorney, Agent, or Firm—Richard J. Hicks

[57] ABSTRACT

An orthopaedic bone cutting jig and alignment frame for facilitating a series of controlled, precise bone cuts to fit selected prosthetic knees which promote bone imgrowth and do not rely upon cement for fixation.

4 Claims, 5 Drawing Figures

ORTHOPAEDIC BONE CUTTING JIG AND ALIGNMENT DEVICE

FIELD OF INVENTION

This invention relates to an orthopaedic bone cutting jig and alignment device designed to facilitate a series of controlled precise bone cuts in a knee bone end, sufficient to provide an accurate precise fit of knee implants used for resurfacing arthroplasty.

RELATION TO OTHER APPLICATIONS

This application is related to the earlier field U.S. application for Letters Patent, Ser. No. 518,479 filed July 29, 1983 and assigned to the assignee of the present invention.

BACKGROUND OF INVENTION

In order to insert prosthetic devices, such as partial or total knee replacements, it is, of course, necessary for the surgeon to remove sufficient bone to make room for the device and to prepare the cut ends of the bone to receive and anchor the prosthetic device. Heretofore, while reasonably accurate cutting was required to obtain a good fit, it could generally be done by a surgeon holding a saw in his hand as any small errors could be corrected by judicious application of the cement used to secure the prosthesis to the bone. Modern techniques, however, which include the use of porous coated prostheses to promote bone ingrowth, do not permit the use of adhesives and hence minor alignment deficiencies cannot be corrected in this way. It becomes critical that the surgeon's bone cuts are accurate to within a few thousandths of an inch and such accuracy is impossible to attain with a hand held saw. Numerous attempts have been made to use a variety of jigs which stabilize the cutting blade in a predetermined direction while the saw is held in the surgeon's hand. Each cut requires a different jig as does each design of prosthesis, of which there are many. Furthermore, the jigs themselves tend to flex the blade during cutting thus reducing the chances for an accurate square cut. In our earlier filed application referred to above, there is described a slide bed device for mounting an orthopaedic saw or other bone cutting device so as to provide three accurately controlled degrees of freedom of movement of the cutting device. The cutting device is slidably mounted on a vertical stand for movement in a vertical plane, and the vertical stand is in turn mounted perpendicularly on two relatively movable horizontal slides at right angles to each other. The horizontal slides are mounted on a three point frame which may be adjustably mounted directly onto the bone to be cut in a plane parallel the longitudinal axis of the bone. While this device solves most of the problems of the prior art, it has been found to require extensive surgical exposure and, furthermore, to require a change in positions of the leg to allow completion of the bone cuts—requiring a fresh set up and re-alignment to be undertaken.

OBJECT OF INVENTION

It is therefore an object of the present invention to provide an improved jig for use in resurfacing arthroplasty.

By one aspect of this invention there is provided a jig for mounting an orthopaedic saw or other suitable bone cutting device comprising:

a frame adjustably mounted on said base and comprising first and second pairs of spaced parallel bars mounted perpendicular to each other at adjacent ends of the respective bars;

means to adjustably and releasably secure each of a patient's tibia and femur to said frame in anatomical and planar parallel alignment with a respective one of said first and second pairs of parallel bars;

planar means releasably mounted on either pair of said parallel bars for sliding movement therealong and extending perpendicularly thereto;

means to releasably lock said bed means to the selected said parallel bars at any selected position thereon; and means slidably mounted on said bed means for movement perpendicular to said selected pair of parallel bars, adapted to receive and releasably secure thereto aid orthopaedic bone butting device.

DESCRIPTION OF DRAWINGS

The invention will be described in more detail hereinafter with reference to the drawings in which.

DETAILED DESCRIPTION OF PREFERRED EMBODIMENTS

Figure 1:
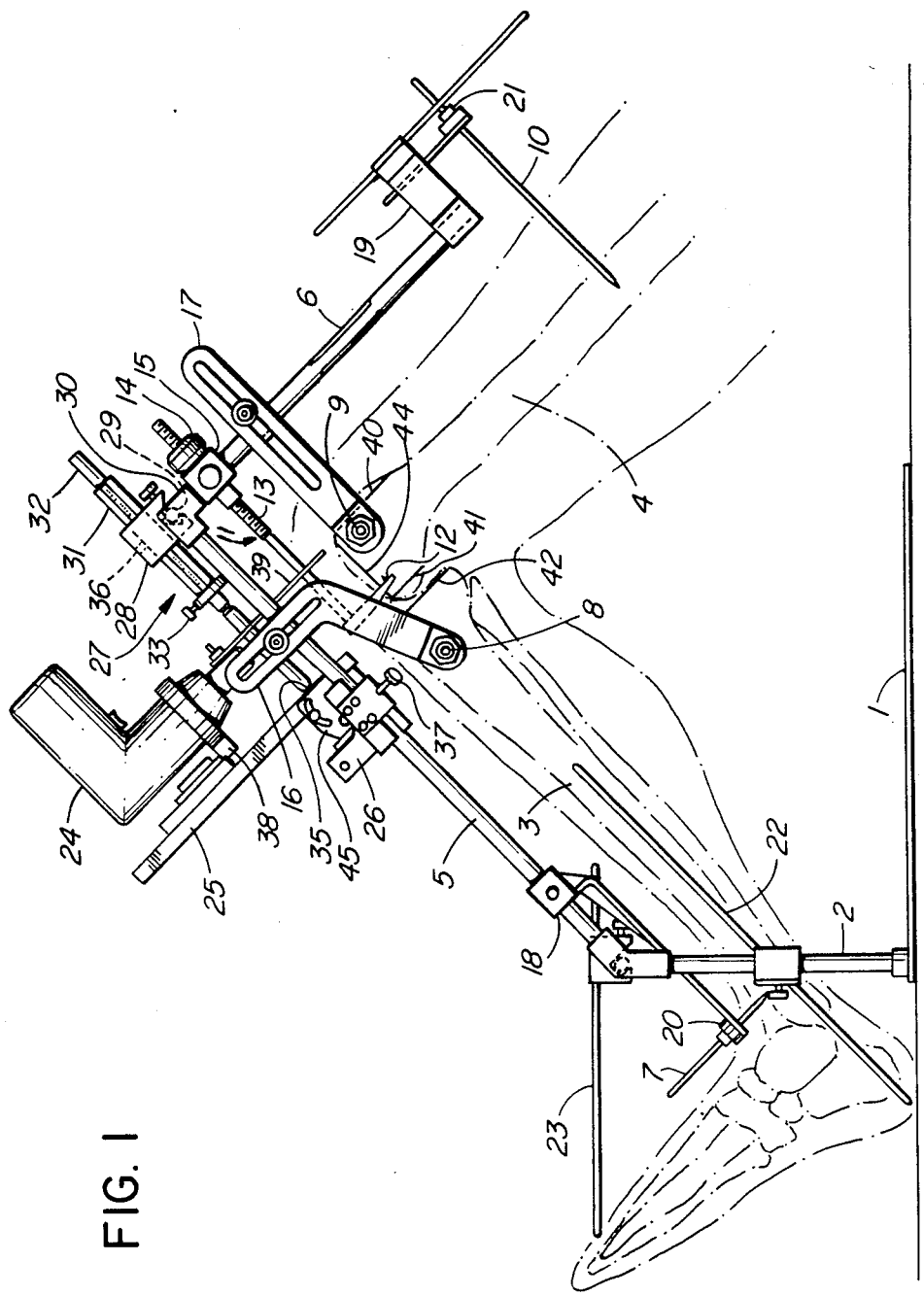
FIG. 1 is a side view of the jig according to one embodiment of the present invention.
Figure 2:
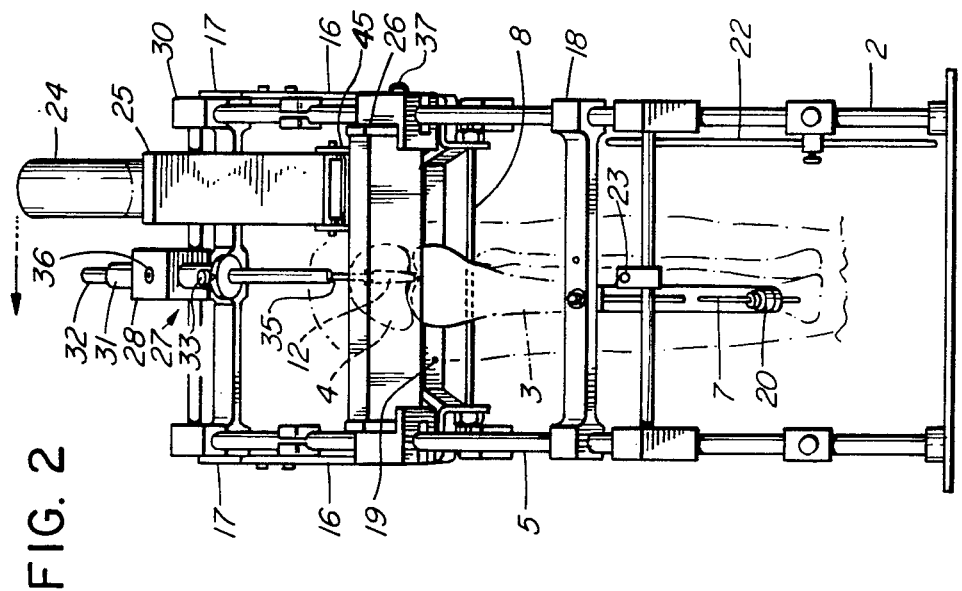
FIG. 2 is a front view of the jig according to the embodiment of the invention shown in FIG. 1.

In contrast to the device in the earlier filed application referred to above, in which the slide bed device is mounted directly on the tibia, the device of the present invention provides, as shown in FIGS. 1 and 2, a horizontal baseplate 1, which is arranged to stand on the operating table, with a vertical stand 2 mounted thereon. The tibia 3 and femur 4 and anatomically aligned in three dimensions with respective parallel pairs of extensions 5, 6 of stand 2 and held in precise alignment therewith by means of bone pins 7, 8, 9 and 10. Parallel pairs of extensions 5, 6 are arranged at right angles to each other, so that the tibia 3 and femur 4 are similarly held at right angles to each other, as seen in side view in FIG. 1. Pins 8 and 9 are transverse bone perforating pins both ends of which are adjustable in three directions by means of brackets 16 and 17 respectively, which brackets are releasably lockable in any desired orientation on extensions 5, and 6 respectively. Pins 7 and 10 are longitudinal bone pins, one end of which is inserted into the lower end of the tibia and upper end of the femur respectively, and the other end of which is adjustable in two directions by means of adjustable arms 18, 19 on extensions 5, 6 respectively. Depth adjustment is provided by screw adjustments 20, 21 respectively at the end of arms 18, 19. Locator comparison arms 22, 23 may be provided to facilitate the alignment process, which ensures that each bone is individually fixed to the respective frame member in precise axial alignment at right angles to each other, with the knee centralized in the middle of the right angle the ankle in the midline distally and with the hip in the midline proximally. The tibia and femur are distracted to a controlled degree, by means of an axial, on-line distracting device 11, adjustably mounted on frame extension 6 and comprising a hook shaped member 12 having a screw threaded shank 13 and an adjusting nut 14 mounted on a block 15 for sliding movement on extension 6. Controlled central on-line distraction of the knee, at a right angle, is achieved when the hook 12 of distracting device 11 is engaged at the distal central aspect of the femur at the attachment point of the posterior cruciate ligament, and the screw nut 14 is tightened against the strain provided by the soft tissue elements holding the bones together, i.e. the co-lateral and cruciate ligaments.

Figure 3:
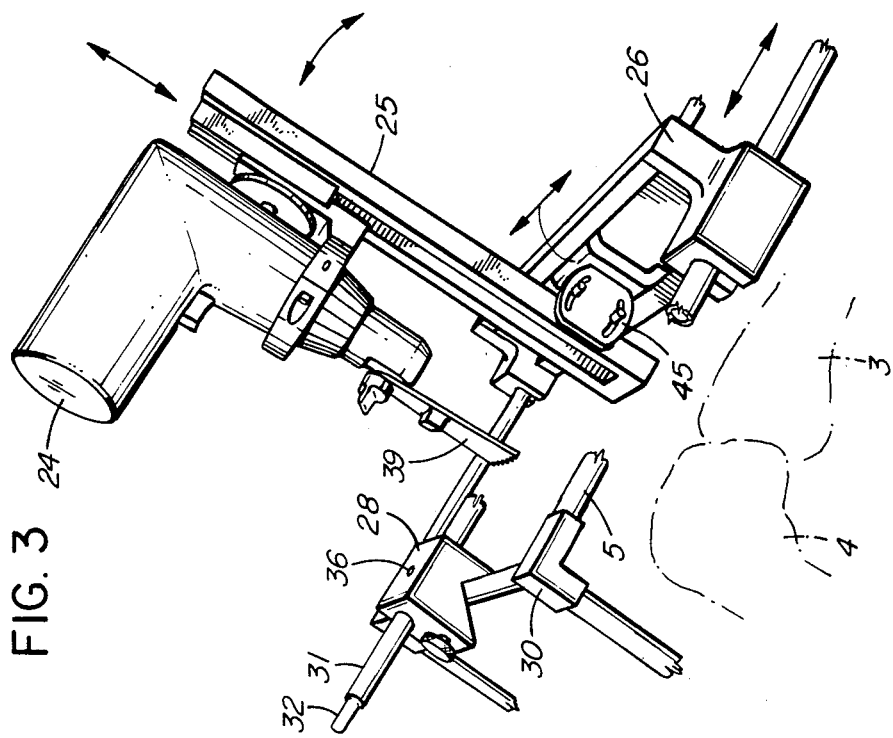
FIG. 3 is a perspective view of the slide bed arrangement.
Figure 4:
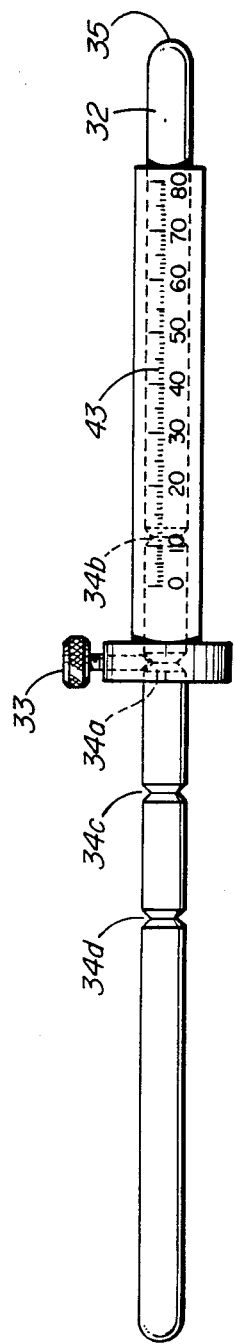
FIG. 4 is a side view of the depth gauge used in the embodiment of FIG. 1.
Figure 5:
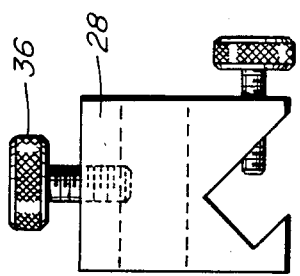
FIG. 5 is a side view of a clamping arrangement for the depth gauge.

The distractor insertion point at the posterior cruciate ligament (PCL) provides the origin reference point for all saw cuts. To facilitate accurate positioning of the saw 24, which is reciprocally slidably mounted as best seen in FIG. 4, on a slide bed 25 which is laterally slidable to a bed 45 between the parallels of bars 5 or 6 and which in turn is mounted on a slidable rack 26, slidably mounted on the parallels of frame 5 or 6 so as to provide 3 degrees of movement for the saw as described in more detail hereinafter. A position gauge 27 (FIG. 3) is provided. Gauge 27 is adjustably mounted in a block 28 on a crosspiece 29 at the right angle junction 30 of extensions 5, 6. Gauge 27 comprises a tube or sleeve member 31 having an axially slidable rod 32 therein. At one end of tube 31 there is provided a spring loaded plunger 33 arranged to engage in preselected slots 34 in rod 32. In order to position the saw, plunger 33 is engaged in PCL origin reference slot 34a and end 35 is manually aligned with the distraction insertion point 12, by sliding tube 31 in block 28 and locking into position with locking screw 36. Plunger 33 can then be withdrawn and rod 32 moved relative to sleeve 31 until the plunger can be reengaged in slot 34b. Slidable rack 26 may then be moved along extension 6 until the surface thereof comes into abutting relation with end 35 of rod 32, and may then be locked into clamping engagement with extension 6 by means of locking screw 37. A standard orthopaedic saw 24, such as a Black and Decker Ortho-Saw, releasably mounted, by means of a quick release clip 38, or slide 25 will now be in position so that the radially oscillating blade 39 thereof is aligned with the femur 4 so as to be able to make the anterior femoral cut 40. Plunger 33 is then withdrawn and rod 32 moved upwardly so that plunger 33 may engage slot 34c. Locking screw 37 is the slackened and slide 25 is moved up until it is again in abutment with end 35 of the necessary rod. Screw 37 is then tightened and the saw is aligned so as to be able to make the posterior femoral cut 41. After this cut is completed the adjustment procedure is repeated with the plunger 33 engaged in slot 34d so as to enable the proximal tibial cut 42 to be made. After cut 42 has been made, the rack 36 is removed from bars 5 and remounted on bars 6. Gauge 27 is rotated through 90° on bar 29 and scale 43 is used to adjust the position of the saw blade as required by the surgeon to accommodate mild to moderate flexion deformities prior to making the distal femoral cut 44.

While there are, of course, several further bone cuts required before final fitting of a knee prosthesis, the four cuts 40, 41, 42 and 44 outlined above are the only "critical" cuts and provided they are made accurately, prefabricated femoral and tibial prostheses should slide readily into position for final securement without further trimming.

It will be appreciated that while the invention has been described herein with particular reference to a radially oscillating orthopaedic saw, the invention is equally applicable with other conventional bone cutting devices such as drills, burrs, millers and borers as well as oscillating saws.

We claim:

1. A jig for mounting an orthopaedic bone cutting device comprising:
a base;
a frame adjustably mounted on said base and comprising first and second pairs of spaced parallel bars mounted perpendicular to each other at adjacent ends of the respective bars;
means to adjustably and releasably secure each of a patient's tibia and femur to said frame in anatomical and planar parallel alignment with a respective one of said first and second pairs of parallel bars;
planar bed means releasably mounted on either pair of said parallel bars for sliding movement therealong and extending perpendicularly thereto;
means to releasably lock said bed means to the selected said parallel bars at any selected position thereon; and
means slidably mounted on said bed means for movement perpendicular to said selected pair of parallel bars, adapted to receive and releasably secure thereto said orthopaedic bone cutting device.

2. A jig as claimed in claim 1 including gauge means mounted on said frame to position said bed means at a preselected position on said parallel bars thereby positioning said cutting device to accurately cut one of said tibia and femur at a preselected position.

3. A jig as claimed in claim 1 or 2 including means adjustably mounted on said frame to selectively and controllably distract said tibia and femur, on line, and retain a perpendicular orientation therebetween.

4. A jig as claimed in claim 1 wherein said bone cutting device is selected from the group consisting of an oscillating saw, radially oscillating saw, a burr, a drill, a miller and a borer.

* * * * *